United States Patent
Luemmen et al.

(10) Patent No.: US 8,183,296 B2
(45) Date of Patent: *May 22, 2012

(54) PESTICIDE PHENYLOXY SUBSTITUTED PHENYLAMIDINE DERIVATIVES

(75) Inventors: Peter Luemmen, Idstein (DE); Klaus Kunz, Düsseldorf (DE); Jörg Greul, Leichlingen (DE); Oliver Guth, Leverkusen (DE); Benoît Hartmann, Saint Foy-lès-Lyon (FR); Kerstin Ilg, Köln (DE); Wahed Ahmed Moradi, Monheim an Rhein (DE); Thomas Seitz, Langenfeld (DE); Darren Mansfield, Bergisch Gladbach (DE); Jean-Pierre Vors, Sainte Foy lès Lyon (FR); Peter Dahmen, Neuss (DE); Arnd Voerste, Köln (DE); Ulrike Wachendorff-Neumann, Neuwied (DE); Marie-Claire Grosjean-Cournoyer, Curis au Mont d'Or (FR); Mark Drewes, Langenfeld (DE); Ralf Dunkel, Lyons (FR); Ronald Ebbert, Nürnberg (DE)

(73) Assignee: Bayer Cropscience AG, Monheim (DE)

( * ) Notice: Subject to any disclaimer, the term of this patent is extended or adjusted under 35 U.S.C. 154(b) by 952 days.

This patent is subject to a terminal disclaimer.

(21) Appl. No.: 12/063,666

(22) PCT Filed: Sep. 12, 2006

(86) PCT No.: PCT/EP2006/066267
§ 371 (c)(1),
(2), (4) Date: Aug. 13, 2008

(87) PCT Pub. No.: WO2007/031508
PCT Pub. Date: Mar. 22, 2007

(65) Prior Publication Data
US 2009/0042994 A1 Feb. 12, 2009

(30) Foreign Application Priority Data
Sep. 13, 2005 (EP) .................................. 05356152

(51) Int. Cl.
*A01N 37/52* (2006.01)
*C07C 257/18* (2006.01)
*C07C 205/06* (2006.01)
*C07C 217/90* (2006.01)
*A01P 3/00* (2006.01)

(52) U.S. Cl. ........ 514/637; 564/247; 564/430; 568/585; 568/939

(58) Field of Classification Search .................. None
See application file for complete search history.

(56) References Cited

U.S. PATENT DOCUMENTS

| 3,284,289 | A | * | 11/1966 | Duerr et al. | 514/238.5 |
| 3,857,836 | A | * | 12/1974 | Horlein et al. | 544/165 |
| 3,867,448 | A | * | 2/1975 | Duerr et al. | 564/245 |
| 4,169,852 | A | * | 10/1979 | Landauer | 564/245 |
| 5,834,494 | A | * | 11/1998 | Ham et al. | 514/339 |
| 7,855,309 | B2 | * | 12/2010 | Kunz et al. | 564/245 |

FOREIGN PATENT DOCUMENTS

| WO | WO 00/46184 | | 8/2000 |
| WO | WO 2004/037239 | * | 5/2004 |

OTHER PUBLICATIONS

Rutherford et al., JACS, 124, 15168-15169, 2002.*
International Search Report No. PCT/EP2006/066267, dated Nov. 7, 2006, 2 pgs.

* cited by examiner

*Primary Examiner* — Kamal Saeed
(74) *Attorney, Agent, or Firm* — Baker Donelson Bearman, Caldwell & Berkowitz, P.C.

(57) ABSTRACT

The present invention relates to 2,5-di-substituted-4-phenyloxy-substituted-phenyl-amidine derivatives of formula (I) in which the substituents are as in the description, their process of preparation, their use as fungicide or insecticide active agents, particularly in the form of fungicide or insecticide compositions, and methods for the control of phytopathogenic fungi or damaging insects, notably of plants, using these compounds or compositions.

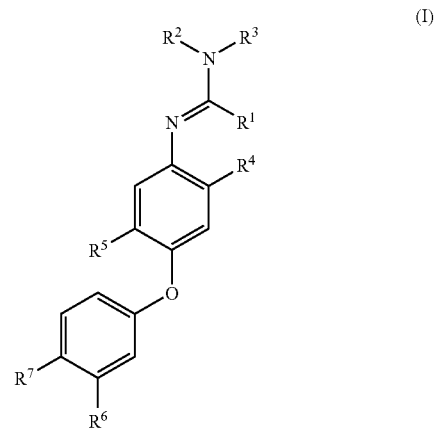

16 Claims, 1 Drawing Sheet

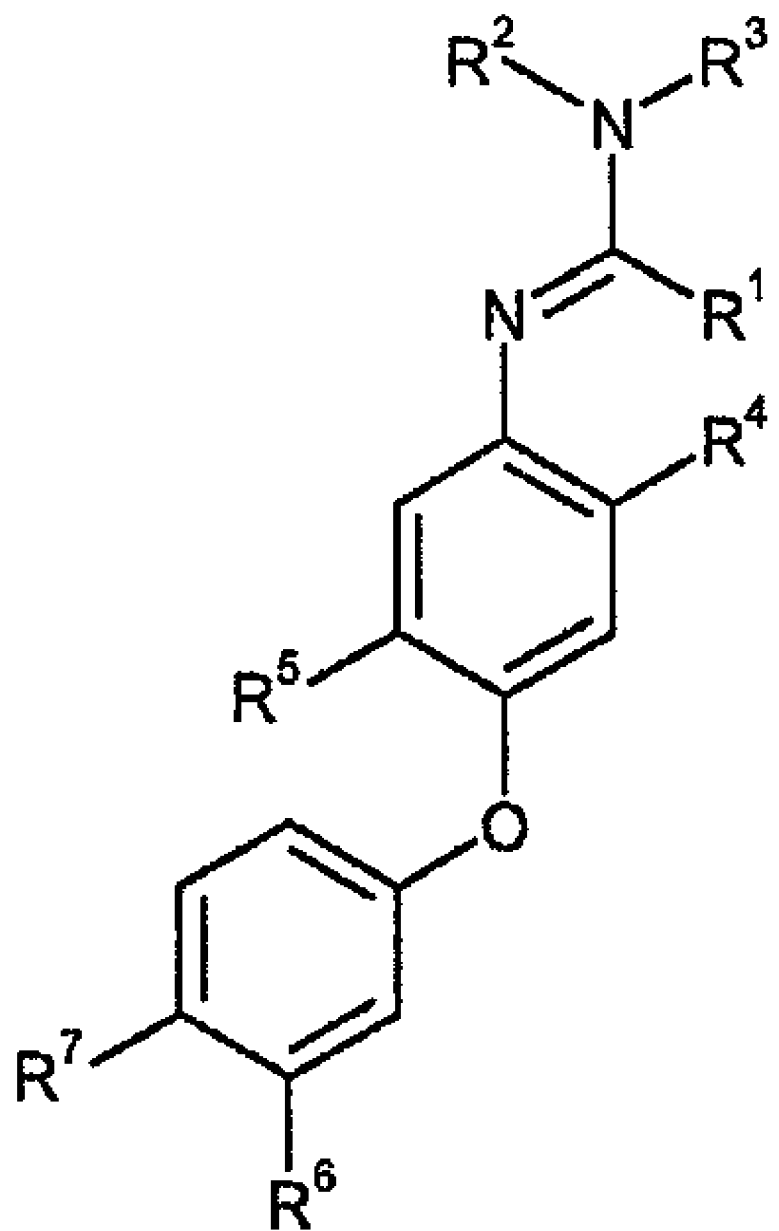
(I)

PESTICIDE PHENYLOXY SUBSTITUTED PHENYLAMIDINE DERIVATIVES

CROSS REFERENCE TO RELATED APPLICATIONS

This is a §371 National Stage Application of International Application No. PCT/EP2006/066267 filed Sep. 12, 2006, which claims priority from European Application No. 05356152.8 filed Sep. 13, 2005.

BACKGROUND OF THE INVENTION

1. Field of the Invention

The present invention relates to 2,5-di-substituted-4-phenyloxy-substituted-phenyl-amidine derivatives, notably to 2,5-dialkyl-4-phenyloxy-substituted-phenyl-amidine derivatives, their process of preparation, their use as fungicide or insecticide active agents, particularly in the form of fungicide or insecticide compositions, and methods for the control of phytopathogenic fungi or damaging insects, notably of plants, using these compounds or compositions.

2. Description of Related Art

In international patent application WO-00/46184 certain phenyl-amidine derivatives are disclosed. However, this document does not specifically disclose nor suggest to select such compounds wherein the phenyl ring is substituted according to the invention thus allowing an unexpected and significantly higher fungicide or insecticide activity.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining an effectiveness at least equivalent to the already known compounds.

In the same way, it is also always of high-interest to use novel insecticide, namatocide or acaricide agents to control damaging insects or other damaging organisms.

SUMMARY OF THE INVENTION

We have now found a new family of compounds which possess the above mentioned effects or advantages.

Accordingly, the present invention provides 2,5-di-substituted-4-phenyloxy-substituted-phenyl-amidine derivatives of formula (I):

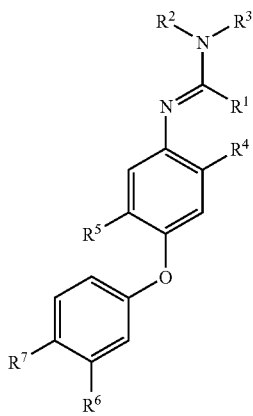

(I)

wherein
$R^1$ represents H, a substituted or non substituted $C_1$-$C_{12}$-alkyl, a substituted or non substituted $C_2$-$C_{12}$-alkenyl, a substituted or non substituted $C_2$-$C_{12}$-alkynyl, SH or a substituted or non substituted S—$C_1$-$C_{12}$-alkyl;
$R^2$ represents a substituted or non substituted $C_1$-$C_{12}$-alkyl;
$R^3$ represents a substituted or non substituted $C_2$-$C_{12}$-alkyl, substituted or non substituted $C_3$-$C_6$-cycloalkyl, substituted or non substituted $C_2$-$C_{12}$-alkenyl, substituted or non substituted $C_2$-$C_{12}$-alkynyl, halogeno-$C_1$-$C_{12}$-alkyl; or
$R^1$ and $R^2$, $R^1$ and $R^3$ or $R^2$ and $R^3$ can form together a substituted or non substituted 5 to 7-membered heterocycle;
$R^4$ represents a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano;
$R^5$ represents H, a substituted or non substituted $C_1$-$C_{12}$-alkyl, a halogen atom, halogeno-$C_1$-$C_{12}$-alkyl, substituted or non substituted O—$C_1$-$C_{12}$-alkyl or cyano
$R^6$ represents a linear or branched $C_1$-$C_6$-alkyl which can be non substituted or substituted by a substituent selected in the list consisting of alkoxy, haloalkoxy, alkylthio and dialkylamino;
$R^7$ represents halogen or cyano;
as well as salts; N-oxydes, metallic complexes, metalloidic complexes and optically active or geometric isomers thereof.

DETAILED DESCRIPTION OF A PREFERRED EMBODIMENT

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

For the compounds according to the invention, halogen means either one of fluorine, bromine, chlorine or iodine and heteroatom can be nitrogen, oxygen or sulphur.

Preferred compounds of formula (I) according to the invention are those wherein $R^1$ represents H; $C_1$-$C_{12}$-alkyl, preferably $C_1$-$C_{12}$-alkyl like methyl and ethyl; or SH.

Other preferred compounds of formula (I) according to the invention are those wherein $R^2$ represents methyl or ethyl.

Still other preferred compounds of formula (I) according to the invention are those wherein $R^3$ represents $C_2$-$C_{12}$-alkyl, preferably a non substituted $C_2$-$C_4$-alkyl like ethyl, n-propyl, i-propyl; $C_2$-$C_{12}$-alkenyl, preferably $C_3$-$C_4$-alkenyl like propenyl or allyl; $C_3$-$C_8$-cycloalkyl like cyclopropyl.

Still other preferred compounds of formula (I) according to the invention are those wherein $R^2$ and $R^3$ can form together a substituted or non substituted 5- to 7-membered heterocycle, preferably a 6-membered heterocycle, more preferably a pipiridinyl or a pyrrolidinyl, even more preferably a bis-alkylated-pyrrolidinyl like a bis-methyl-pyrrolidinyl.

Still other preferred compounds of formula (I) according to the invention are those wherein $R^4$ represents a $C_1$-$C_{12}$-alkyl, preferably a non substituted $C_1$-$C_{12}$-alkyl like methyl and ethyl; a halogen atom like a chlorine atom.

Still other preferred compounds of formula (I) according to the invention are those wherein $R^5$ represents a $C_1$-$C_{12}$-alkyl, preferably a non substituted $C_1$-$C_{12}$-alkyl like methyl and ethyl; a halogen atom like a chlorine atom.

Still other preferred compounds of formula (I) according to the invention are those wherein $R^6$ represents a linear or branched $C_1$-$C_6$-alkyl, preferably $R^6$ is selected in the list consisting of methyl, ethyl, n-propyl, i-propyl, t-butyl, n-butyl, i-butyl, s-butyl.

preferred features of $R^5$ with preferred features of $R^1$ to $R^7$;
preferred features of $R^6$ with preferred features of $R^1$ to $R^7$.

In these combinations of preferred features of the substituents of the compounds according to the invention, the said preferred features can also be selected among the more preferred features of each of $R^1$ to $R^7$ and A so as to form most preferred subclasses of compounds according to the invention.

The present invention also relates to a process for the preparation of compounds of formula (I). Generally, the preparation of compound of formula (I) according to the invention can be carried out as illustrated by scheme 1.

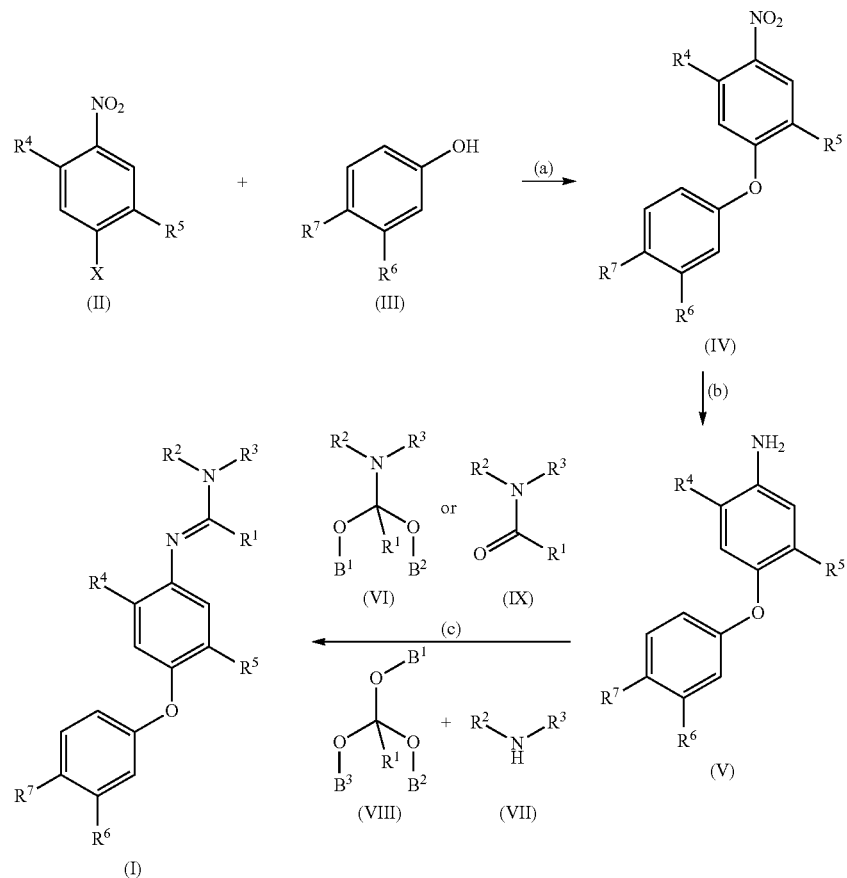

Still other preferred compounds of formula (I) according to the invention are those wherein $R^7$ represents halogen, preferably F, Cl or Br.

The above mentioned preferences with regard to the substituents of the compounds according to the invention can be combined in various manners. These combinations of preferred features thus provide sub-classes of compounds according to the invention. Examples of such sub-classes of preferred compounds according to the invention can combine:

preferred features of $R^1$ with preferred features of $R^2$ to $R^7$;
preferred features of $R^2$ with preferred features of $R^1$ to $R^7$;
preferred features of $R^3$ with preferred features of $R^1$ to $R^7$;
preferred features of $R^4$ with preferred features of $R^1$ to $R^7$;

Nitrophenylether derivatives of formula (IV) can be obtained according to process (a) by reacting nitrobenzene derivatives of formula (II)

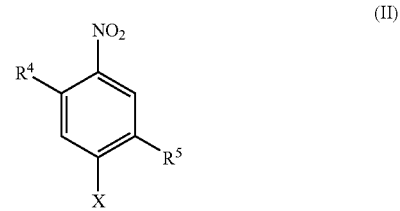

wherein $R^4$ and $R^5$ are as herein-defined;

X represents halogen, triflate, SOMe, mesylate or tosylate;

with phenole derivatives of formula (III)

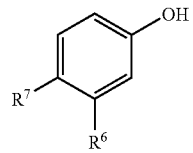

(III)

wherein $R^6$ and $R^7$ are as herein-defined.

Process (a) according to the invention can further comprise one or more of the following characteristics:

presence of a base;

presence of an inert organic diluent;

presence of a catalyst.

Phenole derivatives of formula (III) are known and can be prepared by known processes.

Aniline derivatives of formula (V) can be obtained according to process (b) by reduction of nitrophenylether derivatives of formula (IV).

Preferably, the reduction reaction is carried out in presence of stannous chloride in concentrated hydrochloric acid.

Amidine derivatives of formula (I) can be obtained according to process (c) by reacting aniline derivatives of formula (V)

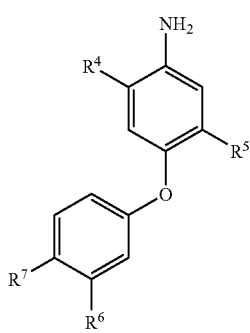

(V)

wherein $R^4$, $R^5$, $R^6$, $R^7$ are as herein-defined.

Various alternatives of process (c) for the preparation of amidine derivatives of formula (I) according to the invention can be considered, they are defined as process (c1), process (c2) and process (c3) according to the invention.

Process (c) according to the invention comprises reacting aniline derivatives of formula (V) with different reagents thus defining processes (c1), (c2) and (c3) respectively.

Process (c1) is carried out further using amino-acetal derivatives of formula (VI)

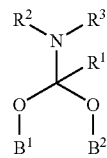

(VI)

wherein $R^1$, $R^2$, $R^3$ are as herein-defined;

$B^1$ and $B^2$ represent each alkyl or together cycloalkyl.

Process (c1) according to the invention can further comprise one or more of the following characteristics:

presence of an acid or a base;

presence of a diluent.

Process (c2) is carried out further using amine derivatives of formula (VII)

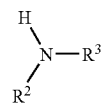

(VII)

wherein $R^2$ and $R^3$ are as herein-defined; in the presence of orthoester derivatives of formula (VIII)

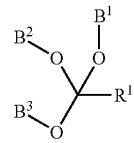

(VIII)

wherein $R^1$ is as herein-defined;

$B^1$, $B^2$ and $B^3$ represent each alkyl.

Process (c3) is carried out further using amide derivatives of formula (IX)

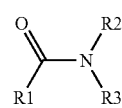

(IX)

wherein $R^1$, $R^2$, $R^3$ are as herein-defined.

Process (c3) according to the invention can further comprise one or more of the following characteristics:

presence of a halogenation agent, like $PCl_5$, $PCl_3$, $POCl_3$, $SOCl_2$;

presence of a diluent.

Suitable diluents for carrying out the processes (a) and (b) according to the invention are all customary inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorobenzene, dichloromethane, chloroform, carbon tetrachloride, dichloroethane or trichloro-ethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; mixtures thereof with water or pure water.

Suitable diluents for carrying out the processes (c1), (c2) and (c3) according to the invention are in each case all customary inert organic solvents. Preference is given to using aliphatic, alicyclic or aromatic hydrocarbons, such as petroleum ether, hexane, heptane, cyclohexane, methyl-cyclohexane, benzene, toluene, xylene or decalin; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethyl-acetamide, N-methylformanilide, N-methylpyrrolidone or hexamethylphosphoric triamide; esters, such as methyl acetate or ethyl acetate; sulphoxides, such as dimethylsulphoxide; or sulphones, such as sulpholane; alcohols, such as methanol, ethanol, n- or iso-propanol, n-, iso-, sec- or tert-butanol, ethanediol, propane-1,2-diol, ethoxyethanol, methoxyethanol, diethylene-glycolmonomethylether, diethyleneglycolmonoethylether; mixtures thereof with water or pure water.

Suitable acid binders for carrying out the processes (a) and (b) according to the invention are all inorganic and organic bases customary for such reactions. Preference is given to using alkaline earth metal or alkali metal hydrides, hydroxides, amides, alcoholates, acetates, carbonates or hydrogen carbonates, such as sodium hydride, sodium amide, lithium diisoproylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, or ammonium carbonate; and also tertiary amines, such as trimethylamine, triethylamine, tributylamine, N,N-dimethylaniline, N,N-dimethyl-benzylamine pyridine, N-methylpiperidine, N-methylmorpholine, N,N-dimethylamino-pyridine, diazabicyclooctane (DABCO), diazabicyclononene (DBN) or di-azabicycloundecene (DBU).

Suitable acid binders for carrying out the processes (b) and (c) according to the invention are in each case all inorganic and organic bases customary for such reactions. Preference is given to using alkaline earth metal or alkali metal hydrides, hydroxides, amides, alcoholates, acetates, fluorides, phosphates, carbonates or hydrogen carbonates, such as sodium hydride, sodium-amide, lithium diisopropylamide, sodium methanolate, sodium ethanolate, potassium tert-butanolate, sodium hydroxide, potassium hydroxide, sodium acetate, sodium phosphate, potassium phosphate, potassium fluoride, caesium fluoride, sodium carbonate, potassium carbonate, potassium hydrogencarbonate, sodium hydrogencarbonate or caesium carbonate; and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylamino-pyridine, diazabicyclooctane (DABCO), diazabicyclononene (DBN) or diazabicycloundecene (DBU).

Suitable acids for carrying out the process (c1) according to the invention are all inorganic and organic acids customary for such reactions. Preference is given to using para-toluene sulfonic acid, methane sulfonic acid, hydrochloric acid (gas, aqueous or organic solution) or sulphuric acid.

Suitable condensing agents for carrying out the process (c3) according to the invention are all condensing agents customary for such amidation reactions. Preference is given to using acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclo-hexylcarbodiimide (DCC) or other customary condensing agents, such as phosphorous pentoxide, polyphosphoric acid, N,N'-carbonyldiimidazole, 2-ethoxy-N-ethoxycarbonyl-1,2-dihydroquinoline (EEDQ), triphenylphosphine/tetrachloromethane or bromo-tripyrrolidino-phosphonium-hexafluorophosphate.

Compounds of formula (I) according to the invention can be prepared according to the herein described processes. It will nevertheless be understood that, on the basis of his general knowledge and of available publications, the skilled worker will be able to adapt these processes according to the specifics of each of the compounds which it is desired to synthesise.

In a further aspect, the present invention also relates to a fungicide or insecticide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention.

This amount can be determined by systematic field trials, which are within the capabilities of a person skilled in the art.

Thus, according to the invention, there is provided a fungicide or insecticide composition comprising, as an active ingredient, an effective amount of a compound of formula (I) as herein-defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the present compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, bait (ready for use), bait concentrate, block bait, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, grain bait, granular bait, granule, hot fogging concentrate, macrogranule, microgranule, oil dispersible powder, oil miscible flowable concentrate, oil miscible liquid, paste, plant rodlet, plate bait, powder for dry seed treatment, scrap bait, seed coated with a pesticide, smoke candle, smoke cartridge, smoke generator, smoke pellet, smoke rodlet, smoke tablet, smoke tin, soluble concentrate, soluble powder, solution for seed treatment, suspension concentrate (=flowable concentrate), tracking powder, ultra low volume (ulv) liquid, ultra low volume (ulv) suspension, vapour releasing product, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity.

The mixtures with other fungicide compounds are particularly advantageous. Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example as CI-respiration inhibitor like diflumetorim
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol, nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phtalide, pyroquilon, tricyclazole;

B12) a compound capable to induce a host defence like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the following list: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamide, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3- pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl] ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxybenzamide, 2-[[[[1-[3(1-Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl) benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compound of formula (I) and the fungicide composition according to the invention can be used to curatively or preventively control the phytopathogenic fungi of plants or crops. Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

In the same manner, the compound of formula (I) and the insecticide composition according to the invention can be used to curatively or preventively control damaging insects, notably of plants or crops. Thus, according to a further aspect of the invention, there is provided a method for curatively or preventively controlling damaging insects, notably of plants or crops, characterised in that a compound of formula (I) or an insecticide composition according to the invention is applied to the seed, the plant or to the fruit of the plant or to the soil wherein the plant is growing or wherein it is desired to grow.

The methods of treatment according to the invention may also be useful to treat propagation material such as tubers or rhizomes, but also seeds, seedlings or seedlings pricking out and plants or plants pricking out. These methods of treatment can also be useful to treat roots. The methods of treatment according to the invention can also be useful to treat the overground parts of the plant such as trunks, stems or stalks, leaves, flowers and fruit of the concerned plant. Among the plants that can be protected by the method according to the invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantains), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the fungicide method according to the invention, mention may be made of:

Powdery mildew diseases such as:
  *Blumeria* diseases, caused for example by *Blumeria graminis;*
  *Podosphaera* diseases, caused for example by *Podosphaera leucotricha;*
  *Sphaerotheca* diseases, caused for example by *Sphaerotheca fuliginea;*
  *Uncinula* diseases, caused for example by *Uncinula necator;*
Rust diseases such as:
  *Gymnosporangium* diseases, caused for example by *Gymnosporangium sabinae;*
  *Hemileia* diseases, caused for example by *Hemileia vastatrix;*
  Phakopsora diseases, caused for example by *Phakopsora pachyrhizi* or *Phakopsora meibomiae;*
  *Puccinia* diseases, caused for example by *Puccinia recondita;*
  *Uromyces* diseases, caused for example by *Uromyces appendiculatus;*
Oomycete diseases such as:
  *Bremia* diseases, caused for example by *Bremia lactucae;*
  *Peronospora* diseases, caused for example by *Peronospora pisi* or *P. brassicae;*
  *Phytophthora* diseases, caused for example by *Phytophthora infestans;*
  *Plasmopara* diseases, caused for example by *Plasmopara viticola;*
  *Pseudoperonospora* diseases, caused for example by *Pseudoperonospora humuli* or *Pseudoperonospora cubensis;*
  *Pythium* diseases, caused for example by *Pythium ultimum;*

Leafspot, leaf blotch and leaf blight diseases such as:
- Alternaria diseases, caused for example by *Alternaria solani;*
- Cercospora diseases, caused for example by *Cercospora beticola;*
- Cladiosporum diseases, caused for example by *Cladiosporium cucumerinum;*
- Cochliobolus diseases, caused for example by *Cochliobolus sativus;*
- Colletotrichum diseases, caused for example by *Colletotrichum lindemuthanium;*
- Cycloconium diseases, caused for example by *Cycloconium oleaginum;*
- Diaporthe diseases, caused for example by *Diaporthe citri;*
- Elsinoe diseases, caused for example by *Elsinoe fawcettii;*
- Gloeosporium diseases, caused for example by *Gloeosponum laeticolor;*
- Glomerella diseases, caused for example by *Glomerella cingulata;*
- Guignardia diseases, caused for example by *Guignardia bidwelli;*
- Leptosphaeria diseases, caused for example by *Leptosphaelia maculans; Leptosphaeria nodorum;*
- Magnaporthe diseases, caused for example by *Magnaporthe grisea;*
- Mycosphaerella diseases, caused for example by *Mycosphaerella graminicola; Mycosphaerella arachidicola; Mycosphaerella fijiensis;*
- Phaeosphaeria diseases, caused for example by *Phaeosphaeria nodorum:*
- Pyrenophora diseases, caused for example by *Pyrenophora teres;*
- Ramularia diseases, caused for example by *Ramularia collo-cygni;*
- Rhynchosporium diseases, caused for example by *Rhynchosporium secalis;*
- Septoria diseases, caused for example by *Septolia apii* or *Septoria lycopercisi;*
- Typhula diseases, caused for example by *Typhula incamata;*
- Venturia diseases, caused for example by *Venturia inaequalis;*

Root and stem diseases such as:
- Corticium diseases, caused for example by *Corticium graminearum;*
- Fusarium diseases, caused for example by *Fusarium oxysporum;*
- Gaeumannomyces diseases, caused for example by *Gaeumannomyces graminis;*
- Rhizoctonia diseases, caused for example by *Rhizoctonia solani;*
- Tapesia diseases, caused for example by *Tapesia acuformis;*
- Thielaviopsis diseases, caused for example by *Thielaviopsis basicola:*

Ear and panicle diseases such as:
- Alternaria diseases, caused for example by *Alternaria* spp.
- Aspergillus diseases, caused for example by *Aspergillus flavus;*
- Cladosporium diseases, caused for example by *Cladosporium* spp.;
- Claviceps diseases, caused for example by *Claviceps purpurea;*
- Fusarium diseases, caused for example by *Fusarium culmorum;*
- Gibberella diseases, caused for example by *Gibberella zeae;*
- Monographella diseases, caused for example by *Monographella nivalis;*

Smut and bunt diseases such as:
- Sphacelotheca diseases, caused for example by *Sphacelotheca reiliana:*
- Tilletia diseases, caused for example by *Tilletia caries;*
- Urocystis diseases, caused for example by *Urocystis occulta;*
- Ustilago diseases, caused for example by *Ustilago nuda;*

Fruit rot and mould diseases such as:
- Aspergillus diseases, caused for example by *Aspergillus flavus;*
- Botrytis diseases, caused for example by *Botrytis cinerea;*
- Penicillium diseases, caused for example by *Penicillium expansum;*
- Sclerotinia diseases, caused for example by *Sclerotinia sclerotiorum;*
- Verticilium diseases, caused for example by *Verticilium alboatrum;*

Seed and soilborne decay, mould, wilt, rot and damping-off diseases:
- Fusarium diseases, caused for example by *Fusarium culmorum;*
- Phytophthora diseases, caused for example by *Phytophthora cactorum;*
- Pythium diseases, caused for example by *Pythium ultimum;*
- Rhizoctonia diseases, caused for example by *Rhizoctonia solani;*
- Sclerotium diseases, caused for example by *Sclerotium rolfsii;*
- Microdochium diseases, caused for example by *Microdochium nivale;*

Canker, broom and dieback diseases such as:
- Nectria diseases, caused for example by *Nectria galligena;*

Blight diseases such as:
- Monilinia diseases, caused for example by *Monilinia laxa;*

Leaf blister or leaf curl diseases such as:
- Taphrina diseases, caused for example by *Taphrina deformans;*

Decline diseases of wooden plants such as:
- Esca diseases, caused for example by *Phaemoniella clamydospora;*
- Eutypa dyeback, caused for example by *Eutypa lata;*
- Dutch elm disease, caused for example by *Ceratocystsc ulmi;*

Diseases of flowers and Seeds such as:
- Botrytis diseases, caused for example by *Botrytis cinerea;*

Diseases of tubers such as:
- Rhizoctonia diseases, caused for example by *Rhizoctonia solani.*

Among the damaging pests or insects that can be controlled at any development stage according to the insecticide method of the invention, mention may be made to:
- the order of the Anoplura (Phthiraptera), for example, *Damalinia* spp., *Haematopinus* spp., *Linognathus* spp., *Pediculus* spp., *Trichodectes* spp.;

the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornitho-doros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;* the class of the Bivalva, for example, *Dreissena* spp.;

the order of the Chilopoda, for example, *Geophilus* spp., *Scutigera* spp.;

the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

the order of the Collembola, for example, *Onychiurus armatus;* the order of the Dermaptera, for example, *Forficula auricularia;* the order of the Diplopoda, for example, *Blaniulus guttulatus;* the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahitia* spp;

the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabeffia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Strongyloides* spp., *Taenia saginata, Taenia solium, Trichinella spiralis, Trichinella nativa, Trichinella* britovi, *Trichinella nelsoni, Trichinella pseudopsiralis, Trichostrongulus* spp., *Trichuris trichuria, Wuchereria bancrofti;*

Protozoa, such as *Elmeria;* the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp;

the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Naso-novia ribisnigri, Nephotettix* spp., *Nilaparvata Jugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phyllo-xera* spp., *Pinnaspis aspidistrae, Planococcus* spp., *Protopulvinaria pyriformis, Pseudaulacaspis pentagona, Pseudococcus* spp., *Psylia* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus arficulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;* the order of the Hymenoptera, for example, *Diprion* spp., *Hoplocampa* spp., *Lasius* spp., *Monomorium pharaonis, Vespa* spp.;

the order of the Isopoda, for example, *Ammadillidium vulgare, Oniscus asellus, Porcellio scaber;* the order of the Isoptera, for example, *Reticulitermes* spp., *Odontotermes* spp.;

the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria;* the order of the Siphonaptera, for example, *Ceratophyllus* spp., *Xenopsylla cheopis.* the order of the Symphyla, for example, *Scutigerella immaculate;* the order of the Thysanoptera, for example, *Ballothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

the order of the Thysanura, for example, *Lepisma saccharina;* the phytoparasitic nematodes including for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp;

the beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;* termites, such as *Kalotermes flavicollis, Cryptotermes brevis, Heterotemes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina;* the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalls, Dermatophagoides pteronissimus, Dermatophagoides forinae;* the order of the Araneae, for example, *Aviculariidae, Araneidae;* the order of the Opiliones, for example, *Pseudoscorpiones chelifer, Pseudoscorpiones cheiridium, Opiliones phalangium;* the order of the Isopoda, for example, *Oniscus asellus, Porcellio scaber;* the order of the Diplopoda, for example, *Blaniulus guttulatus, Polydesmus* spp.;

the order of the Chilopoda, for example, *Geophilus* spp.;

the order of the Zygentoma, for example, *Ctenolepisma* spp., *Lepisma saccharina, Lepismodes inquilinus;* the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa;* the order of the Saltatoria, for example, *Acheta domesticus;* the order of the Dermaptera, for example, *Forficula auricularia;* the order of the Isoptera, for example, *Kalotermes* spp., *Reticulitermes* spp;

the order of the Psocoptera, for example, *Lepinatus* spp., *Liposcelis* spp;

the order of the Coleoptera, for example, *Anthrenus* spp., *Attagenus* spp., *Dermestes* spp.; *Latheticus oryzae, Necrobia* spp., *Ptinus* spp., *Rhizopertha dominica, Sitophilus granarius, Sitophilus oryzae, Sitophilus zeamais, Stegobium paniceum.* the order of the Diptera, for example, *Aedes aegypti, Aedes albopictus, Aedes* taeniorhynchus, *Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa;* the order of the Lepidoptera, for example, *Achroia grisella, Galleria mellonella, Plodia interpunctella, Tinea cloacella, Tinea pellionella, Tineola bisselliella;* the order of the Siphonaptera, for example, *Ctenocephalides canis, Ctenocephalides felis, Pulex irritans, Tunga penetrans, Xenopsylla cheopis.* the order of the Hymenoptera, for example, *Camponotus herculeanus, Lasius fuliginosus, Lasius niger, Lasius umbratus, Monomorium pharaonis, Paravespula* spp., *Tetramorium caespitum;* the order of the Anoplura, for example, *Pediculus humanus capitis, Pediculus humanus corporis, Pemphigus* spp., *Phylloera vastatrix, Phthirus pubis;* the order of the Heteroptera, for example, *Cimex hemipterus, Cimex lectularius, Rhodinus prolixus, Triatoma infestans.*

The fungicide or insecticide composition according to the invention may also be used against fungal diseases or damaging insects liable to grow or attack on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide or insecticide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following tables of compounds examples. The following tables illustrate in a non-limiting manner examples of compounds according to the invention.

In the following examples, M+1 (or M−1) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following examples, the logP values were determined in accordance with EEC Directive 79/831 Annex V.A8 by HPLC (High Performance Liquid Chromatography) on a reversed-phase column (C 18), using the method described below:
Temperature: 40° C.; Mobile phases: 0.1% aqueous formic acid and acetonitrile; linear gradient from 10% acetonitrile to 90% acetonitrile.
Calibration was carried out using unbranched alkan-2-ones (comprising 3 to 16 carbon atoms) with known logP values (determination of the logP values by the retention times using linear interpolation between two successive alkanones).

The lambda max values were determined in the maxima of the chromatographic signals using the UV spectra from 190 nm to 400 nm.

Preparation Example 1

N-Ethyl-N-methyl-N'-[4-(3-t-butyl-4-chlorphenoxy)-5-chloro-2-methylphenyl]formamidine—Compound of Formula (I)

0.37 g (1.16 mmol) of 4-(3-t-butyl-4-chlorphenoxy)-5-chloro-2-methylaniline were dissolved in 2.5 ml of toluene and treated with 0.28 g of a solution of N-ethyl-N-methylformamiddimethylacetal in methanol (60%). The reaction mixture was stirred at 45° C. for 12 h before the reaction mixture was filtrated and the solvent removed in vacuo to yield 444 mg (87% yield, 89% purity) of product; log P (pH 2.3)=2.80.

Preparation of Starting Material 4-(3-t-butyl-4-chlorohenoxy)-5-chloro-2-methylaniline—Compound of Formula (V)

A solution of 3.00 g (8.47 mmol) of 4-(3-t-butyl-4-chlorphenoxy)-5-chloro-2-methylnitrobenzene in 40 ml of dioxane and 40 ml of hydrochloric acid was treated with 5.73 g (25.4 mmol) of stannous chloride at room temperature. The reaction mixture was heated to reflux for 2 hrs, cooled to room temperature, neutralized with aeq. NaHCO3, extracted several times with dichloromethane, dried over $Na_2SO_4$, filtrated and evaporated. Yield: 2.34 g (90.5% purity, 77.1% yield); log P (pH 2.3)=5.68.

4-(3-t-butyl-4-chlorphenoxy)-5-chloro-2-methylnitrobenzene—Compound of Formula (IV)

A mixture of 3.65 g (19.8 mmol) of 3-t-butyl-4-chlorophenol, 3.41 g (18.0 mmol) of 4-chloro-2-fluoro-5-nitrotoluene and 3.73 g (27.0 mmol) of potassium carbonate in 20 ml of dimethyl formamide was stirred at 100° C. for 6 hrs, treated with 50 nl of water at 0° C. and the resulting mixture was stirred for 15 min. The precipitate was separated, washed with hexane and dried in vacuo to yield 5.49 g (91.1% purity, 78.4% yield) of product; log P (pH 2.3)=6.32.

Preparation Example 2

N-Ethyl-N-methyl-N'-[4-(3-t-butyl-4-chlorphenoxy)-2,5-xylyl]formamidine—Compound of Formula (I)

15.20 g (50 mmol) of 4-(3-t-butyl-4-chlorphenoxy)-2,5-xylidine were refluxed in 50 ml of trimethylformiate for 4 h. The reaction mixture was cooled to room temperature and the solvent was removed in vacuo. The residue was dissolved in 200 ml of dichloromethane and subsequently treated with 4.73 g (80 mmol) of N-ethyl-N-methylamine. After stirring at room temperature for 16 h the solvent and unreacted amine was removed in vacuo to give the crude product which was purified by HPLC to yield 13.00 g (68.5% yield, 98.3% purity) of product; log P (pH 2.3)=3.04.

Preparation of Starting Material 4-(3-t-butyl-4-chlorphenoxy)-2,5-xylidine—Compound of Formula (V)

A solution of 40 g (119 mmol) of 4-(3-t-butyl-4-chlorphenoxy)-2,5-dimethylnitrobenzene in 30 ml of n-propanol was treated dropwise with hydrazine hydrate (17.3 ml, 356 mmol), then Pd/C was added (5% on charcoal, 400 mg, 0.2 mmol of Pd) and the mixture was heated to reflux for 10 hrs. After cooling to room temperature the mixture was filtrated, the residue was washed with methanol and the combined filtrates were evaporated. The residue was dissolved in dichloromethane, and the solution was extracted several times with water in order to remove remaining n-propanol. The organic phase was dried over $Na_2SO_4$, filtrated and evaporated. Yield: 32 g (87%); log P (pH 2.3)=4.38.

4-(3-t-butyl-4-chlorphenoxy)-2,5-dimethylnitrobenzene—Compound of Formula (IV)

To a solution of 27.4 g (148 mmol) 3-tBu-4-Cl-phenol and 25 g (135 mmol) 2,5-dimethyl-4-chloro-nitrobenzene in 250 ml of DMF were added 24.2 g (175 mmol) of $K_2CO_3$ and the reaction mixture was heated to reflux for 3 hrs. Further 8 g (58 mmol) of $K_2CO_3$ were added and heating was continued for another 2 hrs. After cooling to room temperature the reaction mixture was poured on 500 ml ice water, the oily product started crystallizing on stirring. The precipitated product was collected by filtration, two more batches were obtained from the mother liquor. Yield: 40 g (89%); log P (pH 2.3)=6.32.

TABLE 1

| example | $R^1$ | $R^2$ | $R^3$ | $R^4$ | $R^5$ | $R^6$ | $R^7$ | $logP_a$ |
|---|---|---|---|---|---|---|---|---|
| 3 | H | Me | Et | Me | Me | iPr | Cl | 2.75 |
| 4 | H | Me | Et | Me | Me | Me | Cl | 2.31 |
| 5 | H | Me | Et | Me | Me | Et | Cl | 2.56 |
| 6 | H | Me | Et | Me | Me | Me | F | M + 1: 315 |
| 7 | H | Me | cycloPr | Me | Me | tBu | Cl | 2.21 |
| 8 | H | Me | nPr | Me | Me | tBu | Cl | 3.30 |
| 9 | H | Me | iPr | Me | Me | tBu | Cl | 3.42 |
| 10 | SH | Me | Et | Me | Me | tBu | Cl | 5.12 |
| 11 | H | Me | nPr | Me | Cl | Et | Cl | 2.84 |
| 12 | H | Me | cycloPr | Me | Cl | Et | Cl | 2.89 |
| 13 | H | Me | Et | Me | Cl | Et | Cl | 2.78 |
| 14 | H | Me | nPr | Me | Me | Et | Cl | 2.76 |
| 15 | H | Me | cycloPr | Me | Me | Et | Cl | 2.71 |
| 16 | H | Me | iPr | Me | Me | Me | Cl | 2.40 |
| 17 | H | Me | nPr | Me | Me | iPr | Br | 2.91 |
| 18 | H | Me | iPr | Me | Me | iPr | Br | 3.34 |
| 19 | H | Me | Et | Me | Me | iPr | Br | 3.04 |
| 20 | H | Me | Et | Me | Cl | iPr | Cl | 2.95 |
| 21 | H | Me | nPr | Me | Cl | iPr | Cl | 3.03 |
| 22 | H | Me | iPr | Me | Cl | iPr | Cl | 3.17 |
| 23 | H | Me | cycloPr | Me | Cl | iPr | Cl | 2.96 |
| 24 | H | Me | cycloPr | Me | Cl | tBu | Cl | 3.24 |
| 25 | H | Me | nPr | Me | Cl | tBu | Cl | 3.27 |
| 26 | H | Me | Et | Me | Cl | tBu | Cl | 3.02 |
| 27 | H | Me | nPr | Me | Me | iPr | Cl | 3.00 |
| 28 | H | Me | iPr | Me | Me | iPr | Cl | 2.74 |
| 29 | SH | Me | Et | Me | Me | iPr | Cl | 4.81 |
| 30 | H | Me | Et | Me | Cl | iPr | Br | 2.84 |
| 31 | H | Me | cycloPr | Me | Cl | iPr | Br | 3.98 |
| 32 | H | Me | iPr | Me | Me | Et | Cl | 2.75 |
| 33 | H | Me | iPr | Me | Cl | iPr | Br | 3.21 |
| 34 | H | Me | nPr | Me | Cl | iPr | Br | 2.91 |
| 35 | SH | Me | Et | Me | Me | tBu | Cl | 5.44 |
| 36 | H | —(CH$_2$)$_5$— | | Me | Cl | tBu | Cl | 3.11 |
| 37 | H | —(CH$_2$)$_5$— | | Me | Cl | Et | Cl | 2.74 |
| 38 | H | Me | Et | Me | CN | iPr | Cl | 2.45 |
| 39 | H | Me | iPr | Cl | Me | tBu | Cl | 3.01 |
| 40 | H | Me | sBu | Me | Me | tBu | Cl | 3.20 |
| 41 | H | Me | sBu | Me | Me | iPr | Cl | 2.98 |
| 42 | H | Me | sBu | Me | Cl | iPr | Cl | 2.90 |
| 43 | H | Me | sBu | Me | Cl | tBu | Cl | 3.19 |
| 44 | H | Me | iPr | Me | Me | Me | F | 2.29 |
| 45 | H | —(CH$_2$)$_5$— | | Me | Me | tBu | Cl | 3.02 |
| 46 | H | Me | Et | Me | Me | tBu—CH$_2$ | Cl | 3.11 |
| 47 | H | Me | Et | Me | Me | Me$_3$Si—CH$_2$ | Cl | 3.01 |
| 48 | H | Me | Et | Me | Me | cycloHex | Cl | 3.18 |
| 49 | H | Me | Et | Cl | Me | Me | Cl | 2.39 |
| 50 | H | Me | iPr | Cl | Me | Me | Cl | 2.48 |
| 51 | H | —(CH$_2$)$_5$— | | Cl | Me | Me | Cl | 2.58 |
| 52 | H | —(CH$_2$)$_4$(CHMe)— | | Cl | Me | Me | Cl | 2.80 |
| 53 | H | —(CH$_2$)$_5$— | | Cl | Me | tBu | Cl | 3.25 |

TABLE 1-continued

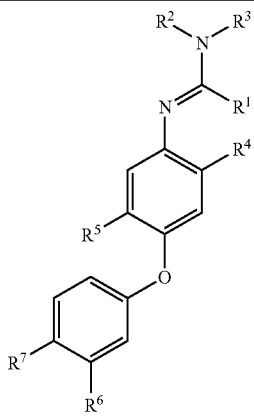

| example | R¹ | R² | R³ | R⁴ | R⁵ | R⁶ | R⁷ | $logP_a$ |
|---|---|---|---|---|---|---|---|---|
| 54 | H | —(CH₂)₄(CHMe)— | | Cl | Me | tBu | Cl | 3.33 |
| 55 | H | Me | Et | Me | Me | nBu | Cl | 2.95 |
| 56 | H | Me | Et | Me | Me | iBu | Cl | 2.92 |
| 57 | H | Me | Et | Me | Me | Me₂(MeO)C | Cl | 2.26 |
| 58 | H | —(CH₂)₅— | | Cl | Me | iPr | Cl | 3.00 |
| 58 | H | Me | iPr | Cl | Me | iPr | Cl | 2.92 |
| 60 | H | Me | Et | Cl | Me | iPr | Cl | 2.78 |
| 61 | H | —(CH₂)₂CF₂(CH₂)₂— | | Me | Me | tBu | Cl | 3.25 |
| 62 | H | —(CH₂)₄(CHMe)— | | Cl | Me | iPr | Cl | 3.07 |
| 63 | H | Me | Et | Me | Br | tBu | Cl | 2.67 |
| 64 | H | Me | Et | Me | Me | cycloPen | Cl | 3.28 |
| 65 | H | —(CH₂)₅— | | Me | Me | tBu—CH₂ | Cl | 3.19 |

Efficacy Example A

In Vivo Preventive Test on *Puccinia recondita* f. Sp. *tritici* (Wheat Brown Rust)

| Solvent: | 50 parts by weight of N,N-dimethylacetamid |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are inoculated with a spore suspension of *Puccinia recondite* in a 0.1% strength aqueous agar solution. After the spray coating has dried on, the plants are sprayed with the preparation of active compound at the stated rate of application. The plants remain for 24 hours in an incubation cabinet at 20° C. and a relative atmospheric humidity of 100%.

The plants are placed in a greenhouse at a temperature of approximately 20° C. and a relative atmospheric humidity of approximately 80% to promote the development of rust pustules.

The test is evaluated 10 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1; 2; 3; 5; 7; 8; 9; 10; 11; 13; 14; 15; 16; 17; 18; 19; 20; 21; 22; 23; 24; 25; 26; 27; 28; 29; 30; 32; 34; 35; 36; 37; 38; 39; 40; 41; 42; 44; 45; 46; 47; 48; 55; 56; 57.

Efficacy Example B

In Vivo Preventive Test on *Erysiphe gramini* (Powdery Mildew on Barley)

| Solvent: | 50 parts by weight of N,N-dimethylacetamid |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has dried on, the plants are dusted with spores of *Erysiphe graminis* f.sp. *hordei*

The plants are placed in a greenhouse at a temperature of approximately 20° C. and a relative atmospheric humidity of approximately 80% to promote the development of mildew pustules.

The test is evaluated 7 days after the inoculation. 0% means an efficacy which corresponds to that of the control, while an efficacy of 100% means that no disease is observed.

In this test the following compounds according to the invention showed an efficacy of 70% or even higher at a concentration of 1000 ppm of active ingredient: 1; 2; 3; 5; 7;

8; 9; 10; 11; 13; 14; 15; 16; 17; 18; 19; 20; 21; 22; 23; 24; 25; 26; 27; 28; 30; 32; 34; 36; 37; 38; 39.

Efficacy Example C

In Vivo Protective Test on *Alternaria solani* (Leaf Spot of Tomato)

| Solvent: | 49 parts by weight of N,N-dimethylformamide |
| Emulsifier: | 1 part by weight of alkylarylpolyglycolether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Alternatia solani*. The plants remain for one day in an incubation cabinet at approximately 20° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control while an efficacy of 100% means that no disease is observed.

In this test, invention related compounds of the following formula revealed an efficacy of 70% or higher at a concentration of 500 ppm of active ingredient: 1; 2; 3; 5; 7; 8; 9; 10; 13; 14; 15; 16; 17; 18; 19; 20; 21; 22; 23; 24; 25; 26; 28; 30; 32.

Efficacy Example D

In Vivo Protective Test on *Podosphaera leucotricha* (Apples)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of apple mildew (*Podosphaera leucotricha*). The plants are then placed in a greenhouse at approximately 23° C. and a relative atmospheric humidity of approximately 70%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 2; 3; 5; 7; 8; 9; 10; 11; 13; 14; 15; 16; 17; 18; 19; 20; 21; 22; 25; 26; 27; 28; 29; 30; 31; 32; 34; 37; 45; 57.

Efficacy Example E

In Vivo Protective Test on *Sahaerotheca fuliginea* (Cucumbers)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protect activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the control, while an efficacy of 100% means that no disease is observed. In this test the compounds according to the invention of the following structures showed efficacy of 70% or even higher at a concentration of 100 ppm of active ingredient: 1; 2; 3; 5; 7; 8; 9; 10; 11; 12; 13; 14; 15; 17; 18; 19; 20; 21; 22; 25; 26; 27; 28; 29; 30; 31; 32; 34; 37; 39; 40; 41; 44; 45.

Efficacy Example F

In Vivo Protective Test on *Uromyces appendiculatus* (Beans)

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of the causal agent of bean rust (*Uromyces appendiculatus*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the control, while an efficacy of 100% means that no disease is observed.

In this test the compounds according to the invention of the following structures showed efficacy of 70% or even higher at a concentration of 100 ppm of active ingredient: 2; 3; 7; 16; 20; 26; 28; 44; 57.

Efficacy Example G

In Vivo Protective Test on *Aedes Aegypti* (AEDSAE U)

| Solvent: | 1% N-methylpyrrolidone (NMP) |
| --- | --- |
|  | 1% diacetonealcohol |
| Dye: | brillantsulfoflavin for staining water |

To produce a suitable preparation of the active compound, the active compound is mixed with the stated amount of solvent, and the concentrate is diluted with staining water to the desired concentration.

*Aedes aegypti* larvae are pipetted with a preparation of active ingredient of the desired concentration.

After the specified period of time, mortality in % is determined. 100% means that all larvae have been killed, a 0% means that none of the larvae have been killed.

In this test, the following compound from the preparation example shows good activity: 3.

Efficacy Example H

In Vivo Protective Test on *Heliothis virescens* (HELIVI U)

| Solvent: | 78 parts by weight acetone |
| --- | --- |
|  | 1.5 parts by weight dimethylformamide |
| Wetting agent | 0.5 parts by weight alkylarylpolyglcolether |

To produce a suitable preparation of the active compound, 1 part by weight of active compound is mixed with the stated amount of solvent and emulsifier, and the concentrate is dilutes with emulsifier-containing water to the desired concentration.

Soybean (*Glycine max.*) leaf sections are sprayed with a preparation of the active ingredient of the desired concentration. Once dry, the leaf sections are infested with eggs of cotton bollworm (*Heliotis virescens*).

After the specified period of time, mortality in % is determined. 100% means that all eggs have been killed and 0% means that none of the eggs have been killed.

In this test for example, the following compound from the preparation examples showed good activity: 18.

Efficacy Example I

In Vivo Protective Test on *Aedes aegypti* (AEDSAE MO)

| Solvent: | 1000 parts by weight dimethylsulfoxid |
| --- | --- |

To produce a suitable preparation of active compound, 1 part by weight of active compound is mixed with the stated amount of solvent, and the concentrate is diluted with water to the desired concentration.

10 to 20 third mosquito larvae (*Aedes aegypti*) are added to the well and incubated.

After the specified period of time, mortality in % is determined. 100% means that all of the larvae have been killed; 0% means that none of the larvae have been killed.

In this test for example, the following compounds from the preparation examples showed good activity: 18.

The invention claimed is:

1. A phenyl-amidine derivative of formula (I):

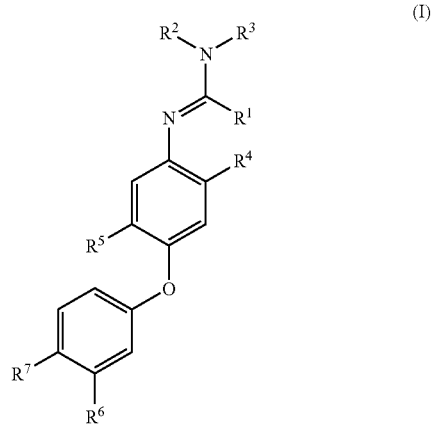

wherein
$R^1$ represents H, a substituted or non-substituted $C_1$-$C_{12}$-alkyl, a substituted or non-substituted $C_2$-$C_{12}$-alkenyl, a substituted or non-substituted $C_2$-$C_{12}$-alkynyl, SH or a substituted or non-substituted S—$C_1$-$C_{12}$-alkyl;
$R^2$ represents a substituted or non-substituted $C_1$-$C_{12}$-alkyl;
$R^3$ represents a substituted or non-substituted $C_2$-$C_{12}$-alkyl, substituted or non-substituted $C_3$-$C_6$-cycloalkyl, substituted or non-substituted $C_2$-$C_{12}$-alkenyl, substituted or non-substituted $C_2$-$C_{12}$-alkynyl, or halogeno-$C_1$-$C_{12}$-alkyl; or
$R^1$ and $R^2$, $R^1$ and $R^3$ or $R^2$ and $R^3$ can form together a substituted or non-substituted 5 to 7-membered heterocycle;
$R^4$ represents a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^5$ represents H, a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^6$ represents methyl, ethyl, n-propyl, i-propyl, t-butyl, n-butyl, i-butyl or s-butyl;
$R^7$ represents halogen or cyano;
or a salt, or an N-oxide, or an optically active or geometric isomer thereof.

2. A compound of formula (I) according to claim 1 wherein
$R^1$ represents H, $C_1$-$C_{12}$-alkyl or SH; or
$R^2$ represents methyl or ethyl; or
$R^3$ represents $C_2$-$C_{12}$-alkyl, $C_2$-$C_{12}$-alkenyl or $C_3$-$C_6$-cycloalkyl; or
$R^2$ and $R^3$ together form a substituted or non-substituted 5 to 7-membered heterocycle; or
$R^4$ represents $C_1$-$C_{12}$-alkyl or a halogen atom; or
$R^5$ represents a $C_1$-$C_{12}$-alkyl or a halogen atom; or
$R^7$ represents a halogen atom.

3. A compound of formula (I) according to claim 1 wherein
$R^1$ represents $C_1$-$C_{12}$-alkyl; or
$R^3$ represents a non-substituted $C_2$-$C_4$-alkyl or $C_3$-$C_4$-alkenyl; or $R^2$ and $R^3$ together form a 6-membered heterocycle; or
$R^4$ represents a non-substituted $C_1$-$C_{12}$-alkyl or a chlorine atom; or
$R^5$ represents a non-substituted $C_1$-$C_{12}$-alkyl or a chlorine atom; or
$R^7$ represents F, Cl or Br.

4. A compound of formula (I) according to claim 1 wherein
$R^1$ represents methyl or ethyl; or
$R^3$ represents ethyl, n-propyl, i-propyl, propenyl, allyl or cyclopropyl; or
$R^2$ and $R^3$ together form a piperidinyl or a pyrrolidinyl; or
$R^4$ represents methyl or ethyl; or
$R^5$ represents methyl or ethyl.

5. A compound of formula (I):

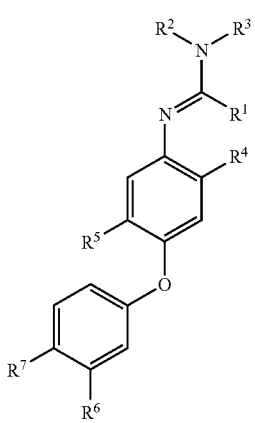

(I)

wherein
$R^1$ represents H, a substituted or non-substituted $C_1$-$C_{12}$-alkyl, a substituted or non-substituted $C_2$-$C_{12}$-alkenyl, a substituted or non-substituted $C_2$-$C_{12}$-alkynyl, SH or a substituted or non-substituted S—$C_1$-$C_{12}$-alkyl;
$R^2$ and $R^3$ form together a bis-alkylated-pyrrolidinyl;
$R^4$ represents a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^5$ represents H, a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^6$ represents a linear or branched $C_1$-$C_6$-alkyl which can be non-substituted or substituted by a substituent selected from the group consisting of alkoxy, haloalkoxy, alkylthio and dialkylamino;
$R^7$ represents halogen or cyano;
or a salt, or an N-oxide, or an optically active or geometric isomer thereof.

6. A compound of formula (I):

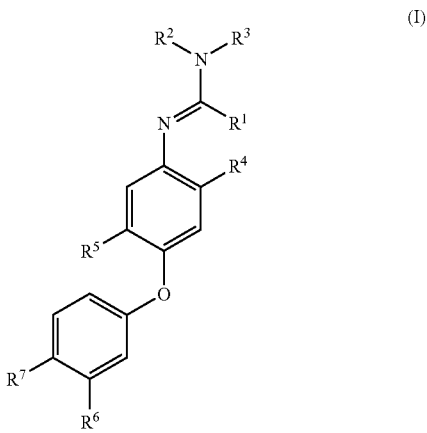

(I)

wherein
$R^1$ represents H, a substituted or non-substituted $C_1$-$C_{12}$-alkyl, a substituted or non-substituted $C_2$-$C_{12}$-alkenyl, a substituted or non-substituted $C_2$-$C_{12}$-alkynyl, SH or a substituted or non-substituted S—$C_1$-$C_{12}$-alkyl;
$R^2$ and $R^3$ form together a bis-methyl-pyrrolidinyl;
$R^4$ represents a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^5$ represents H, a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
$R^6$ represents a linear or branched $C_1$-$C_6$-alkyl which can be non-substituted or substituted by a substituent selected from the group consisting of alkoxy, haloalkoxy, alkylthio and dialkylamino;
$R^7$ represents halogen or cyano;
or a salt, or an N-oxide, or an optically active or geometric isomer thereof.

7. A process for the preparation of a compound of formula (I) according to claim 1 comprising at least one the following steps:

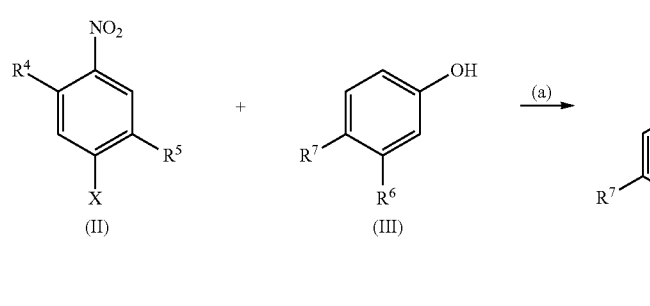

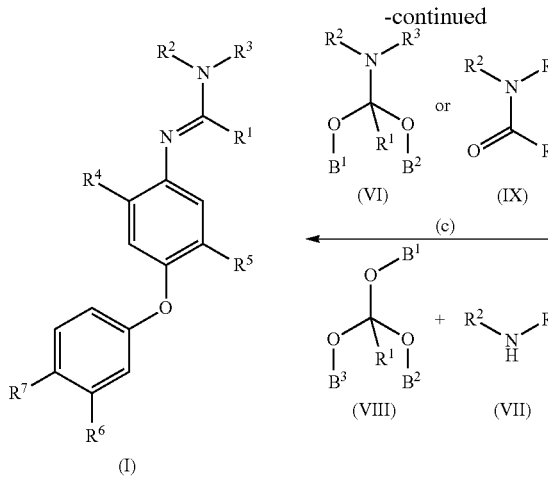

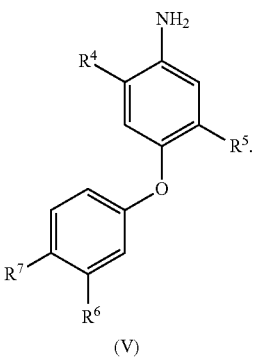

8. A Nitrophenylether derivative of formula (IV)

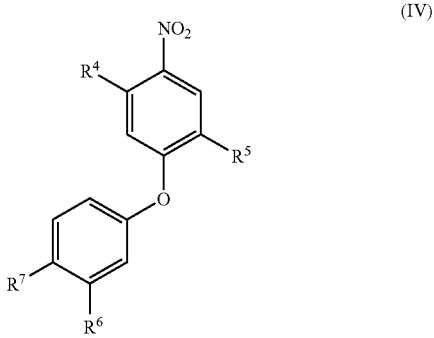

wherein
R$^4$ represents a substituted or non-substituted C$_1$-C$_{12}$-alkyl, a halogen atom, halogeno-C$_1$-C$_{12}$-alkyl, substituted or non-substituted O—C$_1$-C$_{12}$-alkyl or cyano;
R$^5$ represents H, a substituted or non-substituted C$_1$-C$_{12}$-alkyl, a halogen atom, halogeno-C$_1$-C$_{12}$-alkyl, substituted or non-substituted O—C$_1$-C$_{12}$-alkyl or cyano
R$^6$ represents a linear or branched C$_1$-C$_6$-alkyl which can be non-substituted or substituted by a substituent selected from the group consisting of alkoxy, haloalkoxy, alkylthio and dialkylamino;
R$^7$ represents halogen or cyano;
or a salt, or an N-oxide, or an optically active or geometric isomer thereof.

9. A aminophenylether derivative of formula (V)

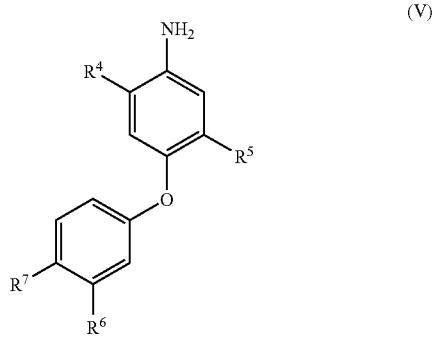

wherein
R$^4$ represents a substituted or non-substituted C$_1$-C$_{12}$-alkyl, a halogen atom, halogeno-C$_1$-C$_{12}$-alkyl, substituted or non-substituted O—C$_1$-C$_{12}$-alkyl or cyano;
R$^5$ represents H, a substituted or non-substituted C$_1$-C$_{12}$-alkyl, a halogen atom, halogeno-C$_1$-C$_{12}$-alkyl, substituted or non-substituted O—C$_1$-C$_{12}$-alkyl or cyano
R$^6$ represents a linear or branched C$_1$-C$_6$-alkyl which can be non-substituted or substituted by a substituent selected from the group consisting of alkoxy, haloalkoxy, alkylthio and dialkylamino;
R$^7$ represents halogen or cyano;
or a salt, or an N-oxide, or an optically active or geometric isomer thereof.

10. A aminoacetal derivative of formula (VI)

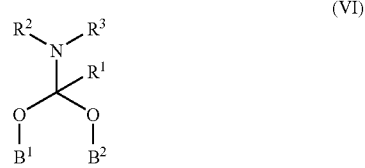

wherein
R$^1$ represents H, a substituted or non-substituted C$_1$-C$_{12}$-alkyl, a substituted or non-substituted C$_2$-C$_{12}$-alkenyl, a substituted or non-substituted C$_2$-C$_{12}$-alkynyl, SH or a substituted or non-substituted S—C$_1$-C$_{12}$-alkyl;
R$^2$ represents a substituted or non-substituted C$_1$-C$_{12}$-alkyl;
R$^3$ represents a substituted or non-substituted C$_2$-C$_{12}$-alkyl, substituted or non-substituted C$_3$-C$_6$-cycloalkyl, substituted or non-substituted C$_2$-C$_{12}$-alkenyl, substituted or non-substituted C$_2$-C$_{12}$-alkynyl, halogeno-C$_1$-C$_{12}$-alkyl; or
R$^1$ and R$^2$, R$^1$ and R$^3$ or R$^2$ and R$^3$ can form together a substituted or non-substituted 5 to 7-membered heterocycle;
B$^1$ and B$^2$ represent each alkyl or together cycloalkyl.

11. A method for controlling phytopathogenic fungi of crops, comprising applying an agronomically effective and substantially non-phytotoxic quantity of a compound according to claim 1 to soil where a plant grows or where a plant is capable of growing, to the leaves and/or fruit of a plant and/or to seed of a plant.

12. A method for controlling damaging insects comprising applying a compound of formula (I):

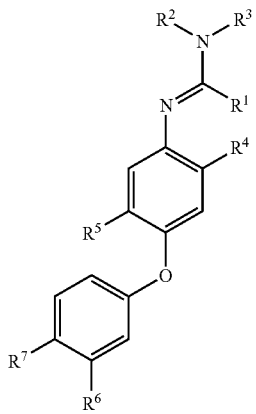

wherein
- $R^1$ represents H, a substituted or non-substituted $C_1$-$C_{12}$-alkyl, a substituted or non-substituted $C_2$-$C_{12}$-alkenyl, a substituted or non-substituted $C_2$-$C_{12}$-alkynyl, SH or a substituted or non-substituted S—$C_1$-$C_{12}$-alkyl;
- $R^2$ represents a substituted or non-substituted $C_1$-$C_{12}$-alkyl;
- $R^3$ represents a substituted or non-substituted $C_2$-$C_{12}$-alkyl, substituted or non-substituted $C_3$-$C_6$-cycloalkyl, substituted or non-substituted $C_2$-$C_{12}$-alkenyl, substituted or non-substituted $C_2$-$C_{12}$-alkynyl, halogeno-$C_1$-$C_{12}$-alkyl; or
- $R^1$ and $R^2$, $R^1$ and $R^3$ or $R^2$ and $R^3$ can form together a substituted or non-substituted 5 to 7-membered heterocycle;
- $R^4$ represents a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
- $R^5$ represents H, a substituted or non-substituted $C_1$-$C_{12}$-alkyl, a halogen atom, halogeno-$C_1$-$C_{12}$-alkyl, substituted or non-substituted O—$C_1$-$C_{12}$-alkyl or cyano;
- $R^6$ represents a linear or branched $C_1$-$C_6$-alkyl which can be non-substituted or substituted by a substituent selected from the group consisting of alkoxy, haloalkoxy, alkylthio and dialkylamino;
- $R^7$ represents halogen or cyano;

or a salt, or an N-oxide, or an optically active or geometric isomer thereof;
- to a seed, a plant and/or to a fruit of a plant and/or to soil wherein the plant is growing or wherein said plant is desired to grow.

13. A compound of formula (I) according to claim 1 wherein
$R^4$ represents a halogen atom.

14. A compound of formula (I) according to claim 1 wherein
$R^4$ represents a halogen atom, halogeno-$C_1$-$C_{12}$-alkyl, substituted or non-substituted O—$C_1$-$C_{12}$-alkyl or cyano.

15. A compound of formula (I) according to claim 1 wherein
- $R^1$ represents a hydrogen atom;
- $R^2$ represents methyl;
- $R^3$ represents ethyl;
- $R^4$ represents a chlorine atom;
- $R^5$ represents methyl;
- $R^6$ represents t-butyl; and
- $R^7$ represents a chlorine atom.

16. A compound of formula (I) according to claim 1 wherein
- $R^1$ represents a hydrogen atom;
- $R^2$ represents methyl;
- $R^3$ represents ethyl;
- $R^4$ represents methyl;
- $R^5$ represents methyl;
- $R^6$ represents t-butyl; and
- $R^7$ represents a chlorine atom.

* * * * *